United States Patent
Stien et al.

(10) Patent No.: US 9,017,327 B2
(45) Date of Patent: Apr. 28, 2015

(54) MEDICAL INSTRUMENT AND METHOD OF PERFORMING A SURGICAL PROCEDURE WITH THE MEDICAL INSTRUMENT

(75) Inventors: Karl Stien, Eau Claire, WI (US); Nathaniel J. Stewart, Eau Claire, WI (US)

(73) Assignee: Stewart and Stien Enterprises, LLC, Eau Claire, WI (US)

( * ) Notice: Subject to any disclaimer, the term of this patent is extended or adjusted under 35 U.S.C. 154(b) by 528 days.

(21) Appl. No.: 13/409,803

(22) Filed: Mar. 1, 2012

(65) Prior Publication Data

US 2013/0231663 A1 Sep. 5, 2013

(51) Int. Cl.
*A61B 18/14* (2006.01)
*A61B 18/00* (2006.01)

(52) U.S. Cl.
CPC ... *A61B 18/1445* (2013.01); *A61B 2018/00184* (2013.01); *A61B 2018/142* (2013.01); *A61B 2018/1422* (2013.01); *A61B 2018/00595* (2013.01); *A61B 2018/00601* (2013.01)

(58) Field of Classification Search
CPC ........... A61B 2018/00184; A61B 2018/00202; A61B 2018/00273; A61B 2018/00279; A61B 2018/00595; A61B 2018/00601; A61B 2018/00607; A61B 2018/142; A61B 2018/1422
USPC .......................................... 606/37, 39–41, 45
See application file for complete search history.

(56) References Cited

U.S. PATENT DOCUMENTS

| | | | |
|---|---|---|---|
| 4,729,374 A * | 3/1988 | Alfranca | 606/171 |
| 4,963,147 A | 10/1990 | Agee et al. | |
| 5,261,906 A | 11/1993 | Pennino et al. | |
| 5,354,296 A | 10/1994 | Turkel | |
| 5,360,428 A | 11/1994 | Hutchinson, Jr. | |
| 5,443,475 A * | 8/1995 | Auerbach et al. | 606/170 |
| 5,460,629 A * | 10/1995 | Shlain et al. | 606/46 |
| 5,569,283 A * | 10/1996 | Green et al. | 606/170 |
| 5,755,723 A * | 5/1998 | Lombardo | 606/170 |
| 5,849,011 A | 12/1998 | Jones et al. | |
| 5,913,866 A * | 6/1999 | Ginn et al. | 606/174 |
| 6,491,691 B1 | 12/2002 | Morley et al. | |
| 6,783,524 B2 | 8/2004 | Anderson et al. | |
| 6,808,525 B2 | 10/2004 | Latterell et al. | |
| 7,276,065 B2 | 10/2007 | Morley et al. | |
| 7,402,162 B2 | 7/2008 | Ouchi | |
| 7,824,398 B2 | 11/2010 | Woloszko et al. | |
| 8,308,725 B2 * | 11/2012 | Bell et al. | 606/52 |
| 8,512,362 B2 * | 8/2013 | Ewers et al. | 606/158 |
| 2003/0040744 A1* | 2/2003 | Latterell et al. | 606/48 |
| 2007/0088351 A1* | 4/2007 | Ewaschuk et al. | 606/45 |
| 2007/0203489 A1* | 8/2007 | Suzuki | 606/51 |

* cited by examiner

*Primary Examiner* — Carl H Layno
*Assistant Examiner* — Eugene Wu
(74) *Attorney, Agent, or Firm* — Wood, Phillips, Katz, Clark & Mortimer

(57) ABSTRACT

A medical instrument having an elongate frame with proximal and distal ends, an operating assembly at a proximal region of the frame, and a working assembly at a distal region of the frame. The working assembly has a cantilevered tip with a free end and is reconfigurable by an operator through the operating assembly by selectively reorienting the tip relative to: a) the frame; and b) a reference plane extending through the frame orthogonally to the central axis at a location on the frame spaced axially from the working assembly toward the operating assembly. The tip in one position projects in a first axial direction toward the reference plane. The working assembly has at least one cautery component that: a) contacts a human body part at the cutting location; and b) is operable to generate a current that dissects a contacted portion of the human body part.

25 Claims, 4 Drawing Sheets

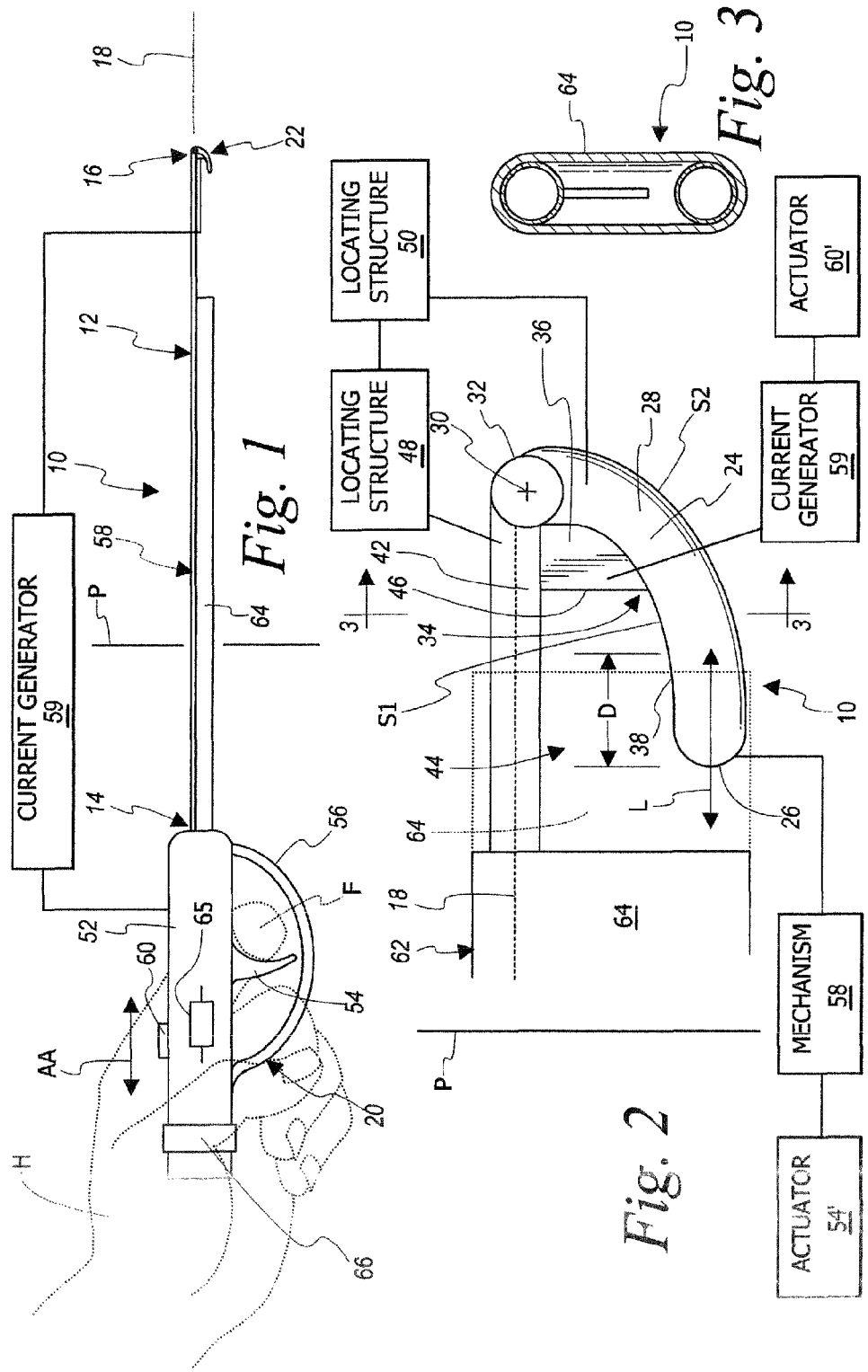

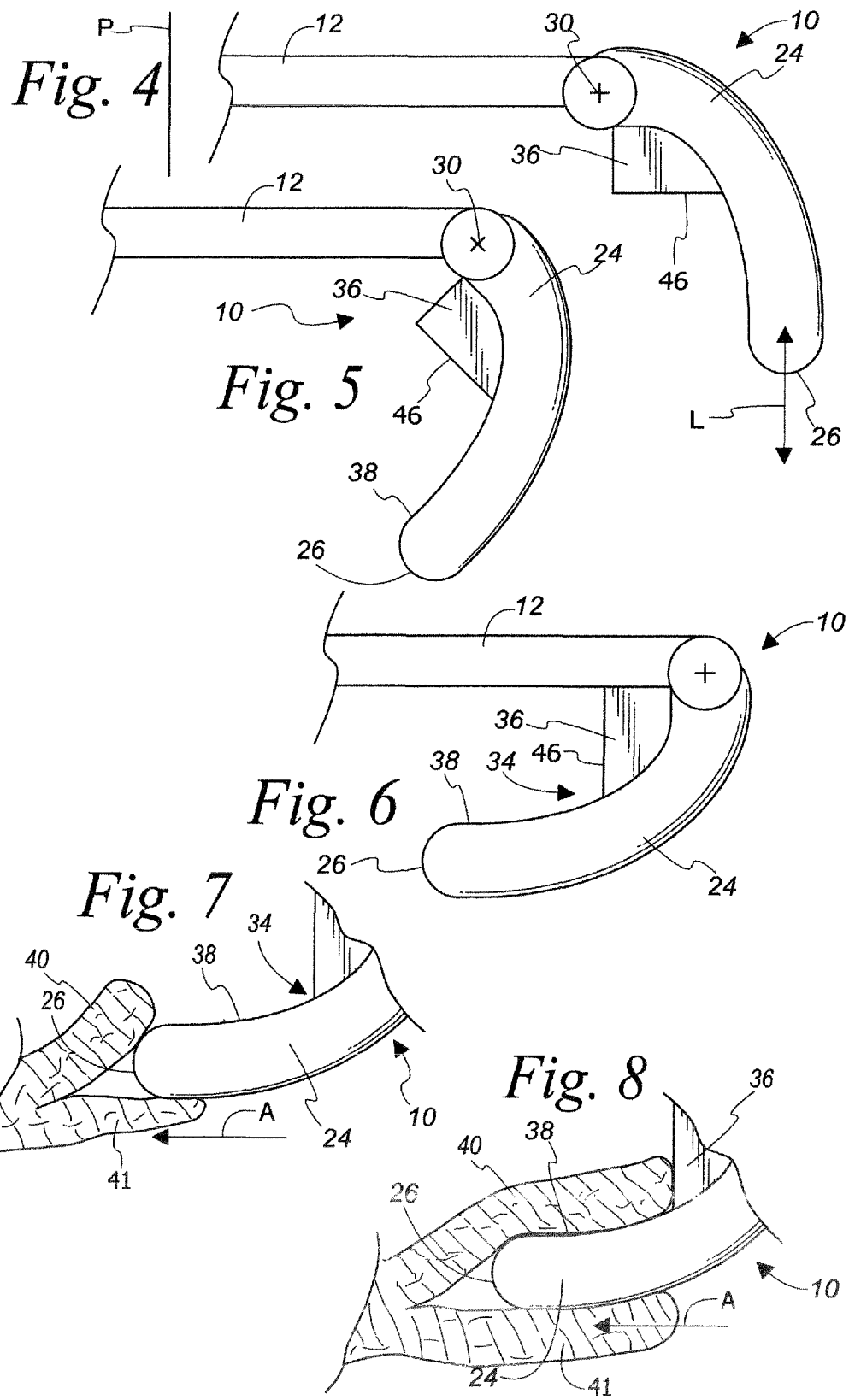

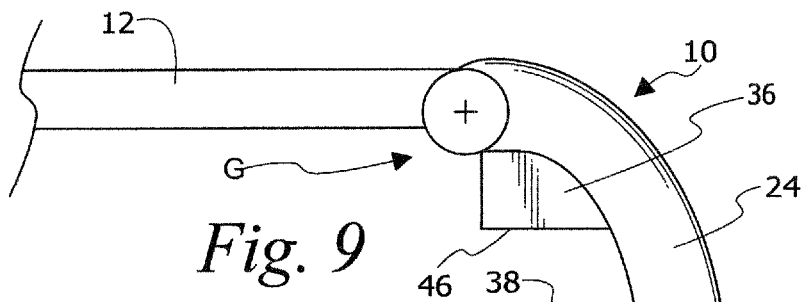
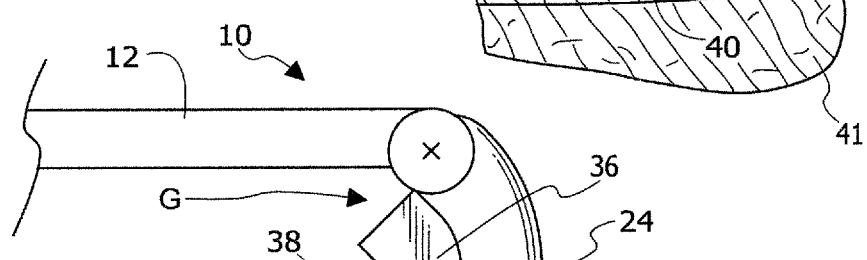
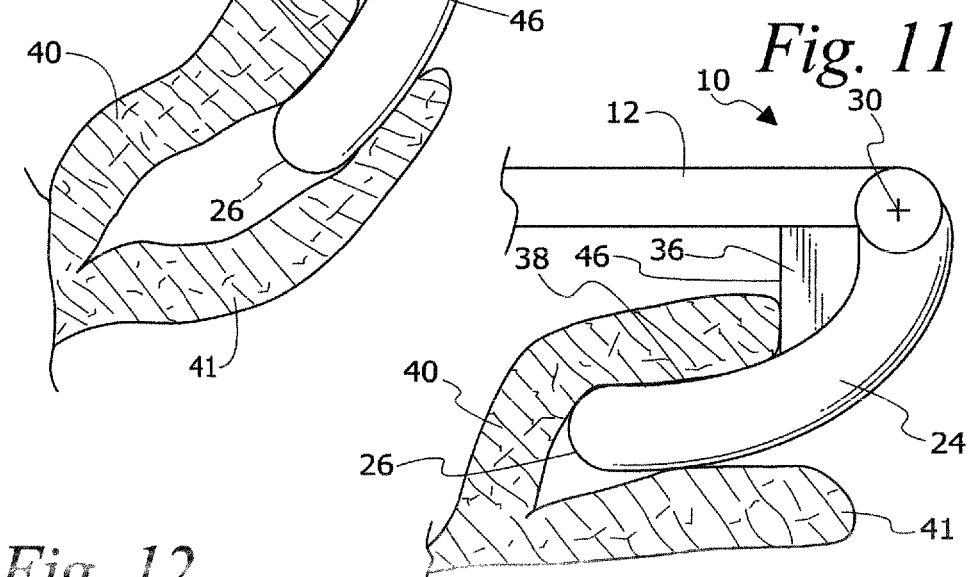

MEDICAL INSTRUMENT AND METHOD OF PERFORMING A SURGICAL PROCEDURE WITH THE MEDICAL INSTRUMENT

BACKGROUND OF THE INVENTION

1. Field of the Invention

This invention relates to medical instruments and, more particularly, to a medical instrument for repositioning human body tissue at an operation site preparatory to cauterization. The invention is also directed to a method of using such a medical instrument.

2. Background Art

In many surgical procedures, tissue is required to be controllably dissected. This dissection is commonly effected using cauterization. Care must always be taken to avoid collateral tissue damage when cauterization is performed.

It is known to use a medical instrument having a repositionable metal tip with an associated cautery device. The tip is controlled to strategically reposition the tissue so that it can be cauterized. Since the cautery device is not electrically isolated from the metal tip, even if care is taken, some collateral tissue damage is likely to occur.

Further, conventional tips are typically configured so that they are at least nominally aligned with the length of an elongate frame that extends between a proximal end, at which the instrument is controlled, and a distal end, at which the tip is provided. An exemplary configuration for this type of device is shown in U.S. Pat. No. 5,360,428, to Hutchinson, Jr. A substantial amount of skill is required to effectively orient the device and balance the tissue to be cauterized on the tip so that the tissue will be contacted precisely where desired by the cautery components and dissected in the desired plane.

Further, Hutchinson, Jr. has limitations in terms of the angle at which the line of the projecting tip is disposed relative to the tissue as the procedure is initiated. Devices exist where tips, such as that in Hutchinson, Jr., have a slight curvature. However, this may not eliminate this problem. A surgeon may still have difficulty repositioning tissue and dissecting it in a required plane. Contending with this problem may undesirably lengthen procedure time.

As one example, this type of instrument is commonly used in arthroscopic hip capsulotomies. With conventional instrumentation, it is difficult for the surgeon to pull the capsule away from the femoral head prior to cutting the capsule, particularly in a plane parallel to the femoral neck. There is a significant risk of collateral damage to the underlying femoral cartilage by the cautery device. Taking the steps and care necessary to minimize this collateral damage potentially increases the time to perform the procedure beyond what is optimally desired and efficient.

SUMMARY OF THE INVENTION

In one form, the invention is directed to a medical instrument having an elongate frame with proximal and distal ends spaced in a lengthwise direction along a central axis of the frame. An operating assembly is at a proximal region of the frame and a working assembly is at a distal region of the frame. The working assembly has a cantilevered tip with a free end and is reconfigurable by an operator through the operating assembly by selectively reorienting the tip relative to a) the frame; and b) a reference plane extending through the frame orthogonally to the central axis at a location on the frame spaced axially from the working assembly toward the operating assembly, in a range between first and second positions. The tip in one position within the range projects in a first axial direction toward the reference plane to allow the tip free end to be engaged with a human body part at an operation site and controllably engaged and moved through the medical instrument guidingly along the tip to a cutting location. The working assembly has at least one cautery component that: a) contacts a human body part at the cutting location; and b) is operable to generate a current that dissects a contacted portion of the human body part at the cutting location.

In one form, the tip free end is rounded and the tip has a surface portion that curves progressively from the tip free end toward the cutting location.

In one form, the tip in another position within the range projects in a line that is substantially parallel to the reference plane.

In one form, there is structure that cooperates between the frame and tip that allows the first and second positions for the tip to be consistently set and releasably maintained.

In one form, the tip is movable into a third position between the first and second positions. Structure cooperates between the frame and tip that allows the third position for the tip to be consistently set and releasably maintained.

In one form, in the first position, the tip projects in a line substantially parallel to and spaced radially from the frame central axis, and in the second position, the tip projects in a line that is substantially parallel to the reference plane.

In one form, the tip is movable between the first and second positions by pivoting relative to the frame about a fixed axis.

In one form, the tip has a body made from a non-metallic material and extending from the free end to the cutting location.

In one form, the tip body has exposed surface portions and substantially all of the exposed surface portions are made from material that is not electrically conductive.

The tip body has exposed surface portions. In one form, substantially all of the exposed surface portions are made from material that is not electrically conductive.

In one form, the operating assembly has a graspable handle portion and an actuator that is operable to change the tip between the first and second positions.

In one form, the actuator is operable by being turned around an axis that is parallel to the central axis of the frame.

In one form, the operating assembly further has a trigger that is engageable by a finger on a hand that is wrapped around the graspable handle portion and movable by the finger to operate the at least one cautery component.

In one form, the medical instrument further includes a cover assembly that can be placed selectively in: a) a covering state wherein the cover assembly extends over at least a portion of the tip; and b) a retracted state.

In one form, the cover assembly in the covering state extends fully around the free end of the tip with the tip in its first position.

In one form, with the tip in the first position the tip projects in a line that is substantially parallel to and spaced radially from the frame central axis so that the frame and tip cooperatively define a "U" shape with spaced legs. The one cautery component extends between the spaced legs.

In one form, the one cautery component has an edge that extends substantially fully between the spaced legs.

In one form, the tip free end is rounded and the tip has a surface portion that curves progressively from the tip free end up to the edge on the cautery component.

In one form, the invention is further directed to a method of performing a surgical procedure. The method includes the step of: a) providing a medical instrument having: an elongate frame with proximal and distal ends spaced in a lengthwise direction along a central axis of the frame; an operating assembly at a proximal region of the frame; and a working assembly at a distal region of the frame. The working assembly has a cantilevered tip with a free end and is reconfigurable by an operator through the operating assembly by selectively reorienting the tip relative to: i) the frame; and ii) a reference plane extending through the frame orthogonally to the central axis at a location on the frame spaced axially from the working assembly toward the operating assembly, in a range between first and second positions. The working assembly further includes at least one cautery component. The method further includes the steps of: b) placing the tip in one position within the range through the operating assembly; c) engaging the tip free end with a human body part; d) at least one of: i) moving the medical instrument relative to the human body part; and ii) repositioning the tip relative to the frame from the one position into another position to thereby cause a portion of the human body part to move guidingly along the tip from the free end to a cutting location wherein the portion of the human body part engages the one cautery component; and e) operating the one cautery component to dissect the portion of the one body part at the cutting location.

In one form, the step of repositioning the tip involves causing the tip to move around a fixed axis relative to the frame.

In one form, the step to repositioning the tip involves repositioning the tip into the another position wherein the tip projects in a line substantially parallel and spaced radially from the frame central axis.

In one form, the method further includes the step of providing a cover assembly and selectively changing the cover assembly between: a) a covering state wherein the cover assembly extends over at least a portion of the tip; and b) a retracted state.

In one form, the step of providing a medical instrument involves providing a medical instrument wherein the tip has a body with exposed surface portions that are made from material that is not electrically conductive.

In one form, the step of providing a medical instrument includes providing a medical instrument wherein the tip has a body with exposed surface portions that are made from material that is not electrically conductive.

BRIEF DESCRIPTION OF THE DRAWINGS

FIG. 1 is a side elevation view of one form of medical instrument, according to the present invention, and made up of an elongate frame with operating and working assemblies, respectively at proximal and distal regions thereof;

FIG. 2 is an enlarged, fragmentary, elevation view of the working assembly on the medical instrument in FIG. 1, and a repositionable tip thereon, with the tip first position;

FIG. 3 is a cross-sectional view of the working assembly taken along line 3-3 of FIG. 2;

FIG. 4 is an enlarged, fragmentary, elevation view of the medical instrument, as in FIG. 2, and showing the tip in a second position;

FIG. 5 is a view as in FIG. 4 with the tip moved to another position between the first and second positions;

FIG. 6 is a view as in FIGS. 4 and 5 with the tip moved from the second position to and past the FIG. 5 position to the first position, as shown also in FIG. 2;

FIG. 7 is an enlarged, fragmentary, elevation view of the medical instrument showing the tip engaging a tissue portion preparatory to cauterization with the tip in the first position, shown in FIGS. 2 and 6;

FIG. 8 is a view as in FIG. 7 wherein the tip and tissue portion have been relatively moved to place the tissue portion at a cutting location against a cautery device on the working assembly while maintaining the tip in the first position;

FIG. 9 is a view as in FIGS. 7 and 8 wherein the tip is placed in the second position upon initially engaging a tissue portion;

FIG. 10 is a view as in FIG. 9 wherein the tip is repositioned to guide the tissue portion towards the cutting location;

FIG. 11 is a view as in FIGS. 9 and 10 wherein the tip is moved to the first position whereby the tissue portion is moved fully to the cutting location;

FIG. 12 is a flow diagram representation of a method of performing a surgical procedure according to the present invention;

DETAILED DESCRIPTION OF THE PREFERRED EMBODIMENT

Figure 13:
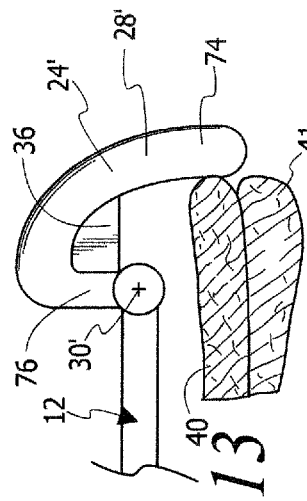
FIGS. 13-15 are views corresponding successively to FIGS. 9-11 and showing a modified form of working assembly, according to the present invention.

In FIGS. 1-11, a medical instrument, according to the present invention, is shown at 10. The medical instrument 10 consists of an elongate frame 12 with proximal and distal ends 14, 16, respectively, spaced in a lengthwise direction along a central axis 18 of the frame 12.

An operating assembly 20 is provided at a proximal region of the frame 12. A working assembly 22 is provided at a distal region of the frame 12.

The working assembly 22 consists of a cantilevered tip 24 with a free end 26. The tip 24 has a body 28. The working assembly 22 is reconfigurable by an operator through the operating assembly 20 by selectively reorienting the tip 24 relative to the frame 12. In the depicted embodiment, the tip body 28 is movable relative to the frame 12 around a fixed axis 30.

The various contemplated positions for the tip 24 can also be clearly described relative to a reference plane P that extends through the frame 12 orthogonally to the central axis 18 at a location on the frame 12 spaced axially from the working assembly 22 toward the operating assembly 20. The location of the reference plane P in FIG. 1 is not limited to what is shown.

The body 28 of the tip 24 has a continuously curved shape/length between the rounded free end 26 and axis 30. The body 28 may be locally narrowed between the free end 26 and axis 30, as shown in dotted lines in FIG. 2, for reasons explained below. While the body 28 has a continuous curve, for purposes of the description and claims herein, the tip 24 will be characterized as "projecting" in a direction that is substantially along a line L, indicated by the double-headed arrow in FIGS. 2 and 4, which is generally parallel to a discrete length of the body 28 extending from the free end 26 a distance D towards the opposite body end 32.

The tip 24 is movable in a range between a first position, as shown in FIG. 2, and a second position, as shown in FIG. 4. The actual range could be less than that shown or greater than that shown, but is preferably selected so that the tip 24 can be placed in at least the first and second positions depicted. As seen in FIG. 4, the tip 24 defines the distalmost extent of the medical instrument 10.

In one position within this range, which is shown in the exemplary form as the first position, the tip 24 projects in a first axial direction toward the reference plane P to allow the tip free end 26 to be engaged, as with a tissue portion at an operation site, and controllably moved through the instrument guidingly along the tip to a cutting location at 34.

The medical instrument 10 is designed to manipulate and dissect tissue and other potentially human body parts. For purpose of the detailed description and claims, "body part" will be used to encompass any part of the human body that can be engaged by the medical instrument, with the depicted or like configuration, so that a portion thereof can be situated at the cutting location 34 whereat it can be dissected, as described below.

At the cutting location 34, at least one cautery component 36 is provided. In this embodiment, there is a single cautery component 36. The cautery component 36 contacts the body part at the cutting location 34 and is operable to generate a current that heats a contacted portion of the human body part at the cutting location 34.

By reason of the shape of the tip body 28, the instrument 10 can be manipulated so as to readily and consistently place a portion of the subject body part predictably at the cutting location 34 in an orientation to dissect across a desired cutting plane. More specifically, the tip body 28 has a surface portion 38 that curves progressively from the convex/rounded tip free end 26 up to the cutting location at 34. This curvature is concave opening toward the central axis 18, as seen in FIG. 2. With the dotted line configuration of FIG. 2, the body 28 is slightly bulbous adjacent to the free end and tapers in diameter away therefrom so as not to inhibit guided sliding movement of a body part portion therealong. The surface portion 38 is also slightly concavely curved over this body length to facilitate this sliding movement of the portion of the body part thereagainst.

As seen in FIGS. 7 and 8, as the tip 24 encounters a body part portion 40, such as tissue, at the operation site, advancement of the instrument 10 in the direction of the arrow A causes the portion 40 to be drawn upwardly, as away from bone and/or another body part portion 41 at the operation site, and move guidingly up the free end 26 to the surface portion 38. Continued advancement of the instrument 10 in the direction of the arrow A causes the portion 40 to arrive at the cutting location 34, whereat it encounters the cautery component 36. In FIGS. 7 and 8, the tip 24 is in the first position therefor, as shown in FIGS. 2 and 6, though the same steps can be performed with the tip 24 in other positions.

The body 28 is preferably made from a material that is not electrically conductive, such as a plastic or other non-metal material, over those surface portions, as shown at S1, S2, that are exposed to potentially contact tissue during procedures. The entire body 28 may be made to be non-conductive where the surfaces therein are exposed and situated to contact tissue in use. Ideally, as the instrument 10 engages body parts during a procedure, the surfaces on the instrument 10 that contact the body parts will not conduct electricity with the cautery component 36 energized. This minimizes the inadvertent infliction of any damage upon any body tissue or other body part other than the body part intended to be contacted by the cautery component 36. Thus, during cauterization, surrounding tissue can be insulated from the cautery component 36 to thereby minimize collateral damage inflicted by heat generated by the energized cautery component 36.

In this embodiment, a distal portion 42 of the frame 12 and the tip body 28 cooperatively define a "U" shape opening axially in a first direction toward the operating assembly 20. With this arrangement, pressure application upon the instrument 10 in the first axial direction causes the body part portion 40 to become captively blocked in a space at 44. The frame portion 42 and tip 24 define spaced legs of the "U" bounding that space 44. The width of the space 44 narrows slightly towards the cutting location with the tip 24 in its first position so that the body part portion 40 is consistently funneled to against the cautery component 36 at the base of the "U". So long as pressure is maintained on the instrument 10 in the direction of the arrow A, the body part portion 40 will not escape from the space 44.

Additionally, the distal portion 42 of the frame 12 can be made with a non-conductive material to be even more certain that no damage will be inflicted upon the body part portion 40 other than at the intended cauterization site. With this construction, the entire "U" shape on the working assembly 22 is electrically insulated as it engages surrounding body parts as the cautery component 36 is brought into contact with a body part region to be cauterized. The cauterization component 36 may be made, as shown, to span between the frame portion 42 and tip 24 to be consistently brought into contact with the body part portion 40 in a desired plane. In the embodiment shown, the cautery component 36 defines a substantially straight edge 46 that engages the body part portion 40 at the cutting location 34. The edge 46 is shown to extend fully and continuously between the tip 24 and frame portion 42. While the edge 46 is shown as straight, this is not a requirement, nor is it a requirement that there be a single component that produces the cauterization energy. Further, the edge 46 need not be continuous as shown.

The process of dissecting the particular body part portion 40 may be initiated with the tip 24 in the first position therefor, as shown in FIG. 6, wherein the line of the tip 24 is substantially parallel to, and spaced radially from, the frame axis 18. Alternatively, the angle of projection of the tip 24 can be changed depending upon the particular application and geometry at the operation site. For example, the projecting line L of the tip 24 may be as shown in FIGS. 4 and 9, representing the aforementioned second position, wherein the tip projecting line is substantially parallel to the reference plane P. The cauterization process could be carried out with this tip position maintained. Alternatively, the tip 24 might be repositioned to a third position, as shown in FIGS. 5 and 10 or back into the first position in FIGS. 4 and 9. As the position of the tip 24 changes, the body part portion 40 is guidingly slid along the surface portion 38 to against the edge 46 at the cutting location 34.

Referring to FIGS. 9-11, with the tip 24 initially in the FIG. 9 position, the free end 26 can be situated at the interface between the body part portions 40, 41. Movement of the tip 24 toward the FIG. 11 position wedges the body part portion 40 away from the body part portion 41, as seen in FIG. 10, until the body part portion 40 is eventually situated to engage the cautery component 36, as seen in FIG. 11.

By reason of making exposed surfaces on the tip 24 non-conductive, the body part portion 41 remains at all times electrically insulated from the cautery component 36.

Cooperating locating structure, shown schematically at 48, 50, may be provided respectively on the frame 12 and tip 24 to allow the first and second positions, and potentially the third and other desired tip positions, to be consistently set and releasably maintained. The cooperating locating structure 48,

50 may be a detent-type of arrangement or take the form of another type of component known to those skilled in the art, or devisable thereby.

The operating assembly 20 is shown to include a graspable handle portion 52 around which a surgeon's fingers can be wrapped to firmly hold the instrument 10 and allow comfortable manipulation thereof. A trigger/actuator 54 is shown in FIG. 1 and is engageable and movable, as in the direction of the arrow AA, by a finger F on the hand H that is wrapped around the graspable handle portion 52 to controllably reposition the tip 24. A U-shaped, protective cage 56 shields the trigger region and the fingers that operate the trigger 54, thereby avoiding an inadvertent contact that might cause an unintended movement of the trigger 54 by the surgeon during a procedure.

A mechanism is shown at 58, partially within the frame 12, for converting movement of the trigger 54 into a force that causes pivoting of the tip 24. Many different suitable mechanisms 58 could be devised by one skilled in the art. Thus there is no need herein to discuss details of such structure.

The invention also contemplates other types of actuators for the mechanism 58, as shown generically at 54' in FIG. 2.

The cautery component 36 is energized by a current generator 59 of conventional construction. The current generator 59 is operable by a switch actuator 60 that is translatable along the line of the double-headed arrow AA between "on" and "off" positions and potentially to vary operating current.

The current generator 59 can be operated through other types of actuators. A generic actuator 60' is shown in FIG. 2 and may be in the form of a foot pedal or other type of mechanism.

Another optional feature is the provision of a cover assembly at 62. The cover assembly 62 consists of a sleeve 64 with a generally oval cross-sectional shape, as shown in FIG. 3, to slide over a portion of the tip 24, with the tip 24 in its first position and the cover assembly 62 in a covering state. The sleeve 64 can be retracted to the solid line position in FIGS. 1 and 2 into a retracted state wherein the tip 24 is fully exposed. The sleeve 64 can be repositioned through an actuator 65 on the handle 52. The actuator 65 is shown as a translatable component engageable and movable by the thumb or a finger on a user's hand H, as along a line indicated by the double-headed arrow AA.

By extending fully around the free end 26 of the tip 24 with the tip 24 in its first position, the direction of the working assembly 22 to the operating site, and withdrawal of the same therefrom, is facilitated without snagging of the tip free end 26, whether the procedure is carried out laparoscopically or through an open incision.

An actuator 66 is shown in FIG. 1 in the form of a ring that is journaled for turning relative to the graspable handle 52 about an axis. This actuator 66 design might be used instead of, or in conjunction with, actuators as previously described for the tip 24, the current generator 59 and the cover assembly 62.

With the medical instrument 10 as depicted, a method of performing a surgical procedure can be carried out as shown in flow diagram form in FIG. 12.

As shown at block 67, a medical instrument is provided, as described above.

As shown at block 68, the tip is engaged with a body part.

As shown in block 70, the tip is repositioned relative to the portion of the body part by: a) moving the medical instrument relative to the body part; and/or b) repositioning the tip relative to the frame from one position into another position to thereby cause a portion of a human body part to move guidingly along the tip from the free end to the cutting location whereat the portion of the human body part engages the at least one cautery component.

As shown at block 72, the one cautery component is operated to dissect the portion of the body part at the cutting location.

As noted previously, the procedure can be carried out as shown in FIGS. 7 and 8 with the tip engaged and repositioned relative to the body part portion without changing the position of the tip relative to the frame. Alternatively, as shown sequentially in FIGS. 9-11, the tip can be reoriented to effect engagement and repositioning of the body part therealong to present the body part portion at the cutting location. In both cases, the portion of the body part is lifted by, and slid along, the tip.

With the tip 24 positioned as in FIGS. 9 and 10, a gap G is produced that potentially could result in a body part being pinched between the cautery component 36 and frame 12 as the tip 24 moves further towards the FIG. 11 position and ultimately into the FIG. 11 position. While this gap G does not necessarily present a problem, the gap G can be eliminated by modifying the tip configuration.

Figure 14:
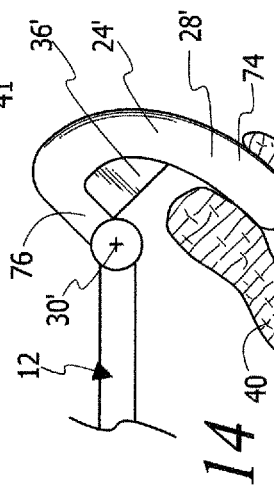
Figure 15:
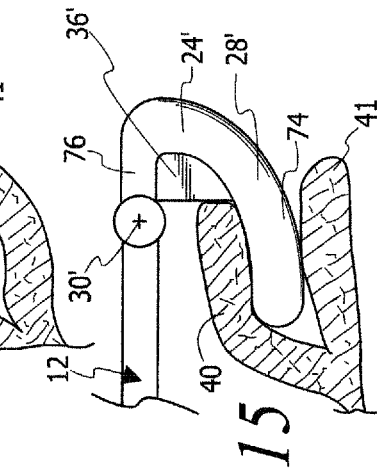

In one modified form, as shown in FIGS. 13-15, a tip 24' is shown with a body 28' having a fixed "U" shape. One leg 74 of the "U" shape defined by the body 28' corresponds to the tip 24, previously described. The other leg 76 is connected to the frame 12 for guided pivoting movement around an axis 30'.

The body 28' is movable between the positions shown in FIGS. 13 and 15, causing the leg 74 to move correspondingly to the tip 24 between the FIG. 4 and FIG. 6 positions.

With the fixed "U" shape, the cautery component 36' is in fixed relationship to, and spans fully between, the legs 74, 76 throughout the range of movement of the body 28'.

As seen in FIGS. 13-15, the leg 74, which becomes a cantilevered "tip", cooperates with the aforementioned body part portions 40, 41 as it is moved between the FIGS. 13 and 15 positions, in the same manner that the tip 24 cooperates with the body part portions 40, 41, as it moves between the FIGS. 9 and 11 positions.

Figure 16:
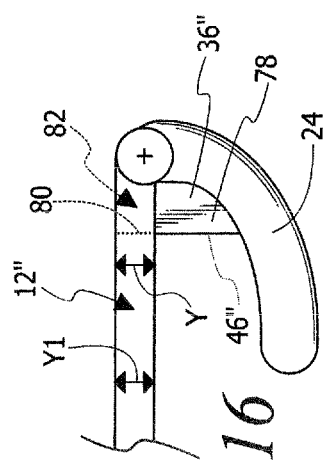
FIG. 16 is a view as in FIG. 11 and showing a modified form of cautery component on the working assembly.

As a further alternative, as shown in FIG. 16, the tip 24 can be used with a modified form of frame 12" and cautery component 36".

The cautery component 36" has a body 78 and a cutting edge 46" thereon with an extended length Y compared to the cautery component 36. The frame 12" has a slot 80 formed therein to accept the extended portion at 82 of the cautery component 36".

Depending upon the dimension Y1 of the frame 12", the aforementioned gap G may be reduced or altogether eliminated using this configuration.

Figure 17:
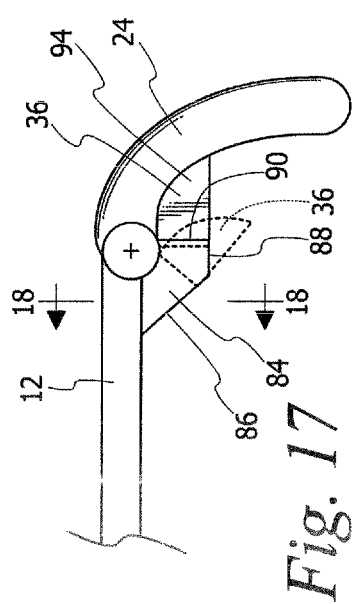
FIG. 17 is a view as in FIG. 9 and showing a modified form of working assembly including a wall that cooperates with a cautery component as the tip thereon is moved over its permissible range.
Figure 18:
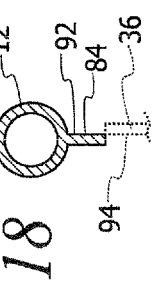
FIG. 18 is a cross-sectional view of the working assembly taken along line 18-18 of FIG. 17.

A still further alternative design is shown in FIGS. 17 and 18. In these Figures, the tip 24, frame 12, and cautery component 36, as described above, are utilized.

A wall 84 is fixed to the frame 12. The wall 84 is generally flat and bounded by straight edges 86, 88, 90 where the wall 84 projects from the frame 12. The plane of one surface 92 of the wall 84 is slightly offset and parallel to a flat surface 94 on the cautery component 36.

The wall 84 may be configured so that the wall 84 and cautery component 36 slide one against the other into different overlapping relationships as the tip 24 is pivoted, thereby to cooperatively span between the tip 24 and frame 12 at all times as the tip 24 is repositioned. Depending upon how the parts are configured, the aforementioned gap G can be either partially or fully eliminated.

The foregoing disclosure of specific embodiments is intended to be illustrative of the broad concepts comprehended by the invention.

The invention claimed is:

1. A medical instrument comprising:
an elongate frame with proximal and distal ends spaced in a lengthwise direction along a central axis of the frame;
an operating assembly at a proximal region of the frame; and
a working assembly at a distal region of the frame,
the working assembly comprising a cantilevered tip with a free end and reconfigurable by an operator through the operating assembly by selectively reorienting the tip relative to: a) the frame; and b) a reference plane extending through the frame orthogonally to the central axis at a location on the frame spaced axially from the working assembly toward the operating assembly, in a range between first and second positions,
the tip in one position within the range projecting in a first axial direction toward the reference plane to allow the tip free end to be engaged with a human body part at an operation site and controllably engaged and moved through the medical instrument guidingly along the tip to a cutting location,
the working assembly comprising at least one cautery component that: a) contacts a human body part at the cutting location; and b) is operable to generate a current that dissects a contacted portion of the human body part at the cutting location,
wherein with the tip in the one position the tip and frame cooperatively define a "U" shape with a base and spaced legs opening in a proximal direction and the at least one cautery component is at the base of the "U" so that tissue can be guided by the "U" shape to and against the at least one cautery component.

2. The medical instrument according to claim 1 wherein there is structure that cooperates between the frame and tip that allows the first and second positions for the tip to be consistently set and releasably maintained.

3. The medical instrument according to claim 2 wherein the tip is movable into a third position between the first and second positions and structure cooperates between the frame and tip that allows the third position for the tip to be consistently set and releasably maintained.

4. The medical instrument according to claim 3 wherein in the first position, the tip projects in a line substantially parallel to and spaced radially from the frame central axis, and in the second position, the tip projects in the line that is substantially parallel to the reference plane.

5. The medical instrument according to claim 4 wherein the tip is movable between the first and second positions by pivoting relative to the frame about a fixed axis.

6. The medical instrument according to claim 1 wherein the operating assembly comprises a graspable handle portion and an actuator that is operable to change the tip between the first and second positions.

7. The medical instrument according to claim 6 wherein the actuator is operable by being turned around an axis that is parallel to the central axis of the frame.

8. The medical instrument according to claim 6 wherein the operating assembly further comprises a trigger that is engageable by a finger on a hand that is wrapped around the graspable handle portion and movable by the finger to operate the at least one cautery component.

9. The medical instrument according to claim 1 wherein the medical instrument further comprises a cover assembly that can be placed selectively in: a) a covering state wherein the cover assembly extends over at least a portion of the tip; and b) a retracted state.

10. The medical instrument according to claim 9 wherein the cover assembly in the covering state extends fully around the free end of the tip with the tip in its first position.

11. The medical instrument according to claim 1 wherein the tip has a body comprising a non-metallic material extending from the free end to the cutting location.

12. The medical instrument according to claim 11 wherein the tip body has exposed surface portions and substantially all of the exposed surface portions are made from material that is not electrically conductive.

13. The medical instrument according to claim 1 wherein the tip free end is rounded and the tip has a surface portion that curves progressively continuously from the tip free end up to the cutting location.

14. The medical instrument according to claim 1 wherein the tip is movable within the range to a position wherein the tip free end defines a distalmost extent of the medical instrument.

15. The medical instrument according to claim 1 wherein the tip has a curved length and is movable within the range to a position wherein the curved length is concave opening toward the central axis of the frame.

16. A method of performing a surgical procedure, the method comprising the steps of:
a) providing the medical instrument of claim 1;
b) placing the tip in a first position within the range through the operating assembly;
c) engaging the tip free end with a human body part;
d) at least one of: i) moving the medical instrument relative to the human body part; and ii) repositioning the tip relative to the frame from the first position into another position to thereby cause a portion of the human body part to move guidingly along the tip from the free end to the cutting location wherein the portion of the human body part engages the one cautery component; and
e) operating the one cautery component to dissect the portion of the one body part at the cutting location.

17. The method of performing a surgical procedure according to claim 16 wherein the step of repositioning the tip comprises causing the tip to move around a fixed axis relative to the frame.

18. The method of performing a surgical procedure according to claim 16 wherein the step of repositioning the tip comprises repositioning the tip into the another position wherein the tip projects in a line substantially parallel and spaced radially from the frame central axis.

19. The method of performing a surgical procedure according to claim 16 further comprising the step of providing a cover assembly and selectively changing the cover assembly between: a) a covering state wherein the cover assembly extends over at least a portion of the tip; and b) a retracted state.

20. The method of performing a surgical procedure according to claim 16 wherein the step of providing a medical instrument comprises providing a medical instrument wherein the tip has a body with exposed surface portions that are made from material that is not electrically conductive.

21. A medical instrument comprising:
an elongate frame with proximal and distal ends spaced in a lengthwise direction along a central axis of the frame;
an operating assembly at a proximal region of the frame; and
a working assembly at a distal region of the frame, the working assembly comprising a cantilevered tip with a free end and reconfigurable by an operator through the operating assembly by selectively reorienting the tip relative to: a) the frame; and b) a reference plane extending through the frame orthogonally to the central axis at a location on the frame spaced axially from the working assembly toward the operating assembly, in a range between first and second positions, the tip in one position within the range projecting in a first axial direction toward the reference plane to allow the tip free end to be engaged with a human body part at an operation site and controllably engaged and moved through the medical instrument guidingly along the tip to a cutting location, the working assembly comprising at least one cautery component that: a) contacts a human body part at the cutting location; and b) is operable to generate a current that dissects a contacted portion of the human body part at the cutting location, wherein with the tip in the first position the tip projects in a line that is substantially parallel to and spaced radially from the frame central axis so that the frame and tip cooperatively define a "U" shape with spaced legs and the one cautery component extends between the spaced legs.

22. The medical instrument according to claim 21 wherein the one cautery component comprises an edge that extends substantially fully between the spaced legs.

23. The medical instrument according to claim 22 wherein the tip free end is rounded and the tip has a surface portion that curves progressively from the tip free end up to the edge on the cautery component.

24. The medical instrument according to claim 21 wherein the tip is movable within the range to a position wherein the tip free end defines a distalmost extent of the medical instrument.

25. The medical instrument according to claim 21 wherein the tip has a curved length and is movable within the range to a position wherein the curved length is concave opening toward the central axis of the frame.

* * * * *